United States Patent

Dury

Patent Number: 6,121,492
Date of Patent: Sep. 19, 2000

[54] METHOD FOR PREPARING 2-TRIFLUORO-METHOXY-ANILINE

[75] Inventor: Michel Dury, Lyons, France

[73] Assignee: Rhodia Chimie, Courbevoie Cedex, France

[21] Appl. No.: 09/424,505

[22] PCT Filed: May 26, 1998

[86] PCT No.: PCT/FR98/01050

§ 371 Date: Nov. 29, 1999

§ 102(e) Date: Nov. 29, 1999

[87] PCT Pub. No.: WO98/54121

PCT Pub. Date: Dec. 3, 1998

[30] Foreign Application Priority Data

May 27, 1997 [FR] France ............................. 97 06483

[51] Int. Cl.[7] .................................................. C07C 209/00
[52] U.S. Cl. .................................................................. 564/417
[58] Field of Search ................................................... 564/417

[56] References Cited

FOREIGN PATENT DOCUMENTS 0 546 391 of 0000 European Pat. Off. .

OTHER PUBLICATIONS

Chemical Abstracts, vol. 55, No. 23, 1961, Columbus, Ohio, US; Abstract No. 23408e, L.M. Yagupolskii: "Synthesis of derivatives of phenyl trifluoromethyl ether", XP002056847 & Zhur. Obshchei Khim, vol. 32, 1961, pp. 915–924., Month Unavailable.

W.A. Sheppard: "Alpha–Fluorinated Ethers. 1–5 1. Aryl Fluoroalkyl Ethers", Journal Of Organic Chemistry., vol. 29, No. 1, 1964, Easton, US, pp. 1–11, XP002056846, p. 9–P. 10., Month Unavailable.

*Primary Examiner*—Samuel Barts
*Attorney, Agent, or Firm*—Burns, Doane, Swecker & Mathis, L.L.P.

[57] ABSTRACT

This invention relates to a method for the preparation of a compound of formula I

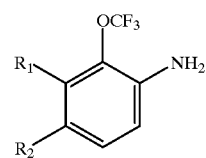

(I)

comprising the steps consisting in:

a) optionally reacting a compound of general formula II:

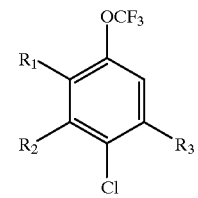

(II)

with a nitration reagent
b) reducing the compound obtained in a)
c) subjecting the compound obtained in b) to a dehydrochlorination in order to obtain the compound of formula I: and
d) isolating the compound obtained in step c) from the reaction mixture.

5 Claims, No Drawings

METHOD FOR PREPARING 2-TRIFLUORO-METHOXY-ANILINE

This application is a 371 of PCT/FR98/0150 filed May 26, 1998.

The invention relates to a method for the preparation of aromatic compounds containing a 2-methoxyaminophenyl group, more particularly 2-trifluoromethoxyaniline.

2-Trifluoromethoxyaniline is an intermediate in the synthesis of many pharmaceutical and agrochemical products.

Various synthetic routes have been proposed.

Several processes using 2-nitrotrifluoro-methoxyphenyl and consisting in reducing it by catalytic hydrogenation or by $SnCl_2$ in acidic medium are thus known. (ZHUR.OBSHCHEI.KHIM. (31) 1961, p. 915–924, (CA C55)23408); J. Org. Chem. (29), 1964, p. 1–11).

Another process described in ZHUR.OBSH-CHEI.KHIM. (31) 1961, p. 915–924 consists in selectively reducing 4-iodo-2-nitrotrifluoro-methoxyphenyl, obtained from 2-nitrotrifluoro-methoxyaniline, in order to obtain 4-iodotrifluoro-methoxyaniline and in hydrogenating this product over Raney nickel.

The present invention provides a novel method for the preparation of aromatic compounds containing a 2-trifluoromethoxyaminophenyl group from aromatic compounds containing a 2-methoxyaminophenyl group.

More precisely, the invention relates to a method for the preparation of a compound of formula I

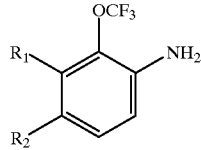

(I)

in which $R_1$ and $R_2$, which may be identical or different, represent a hydrogen atom, a $C_1$–$C_6$ alkyl group, or $R_1$ and $R_2$, taken together with the carbon atoms to which they are attached, represent a $C_6$–$C_{10}$ aryl group; comprising the following steps:

a) optionally reacting a compound of general formula II:

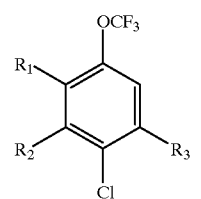

(II)

in which $R_1$, $R_2$ and $R_3$ represent the above values or $R_1$ represents a hydrogen atom or a $C_1$–$C_6$ alkyl group and at least one from among $R_2$ and $R_3$ represents a chlorine atom, the other being a hydrogen atom or a $C_1$–$C_6$ alkyl group, or $R_1$ and $R_2$, taken together with the carbon atom to which they are attached, represent a $C_6$–$C_{10}$ aryl ring, and $R_3$ represents a hydrogen atom, a $C_1$–$C_6$ alkyl group or a chlorine atom, with a nitration reagent in order to form a compound of formula III:

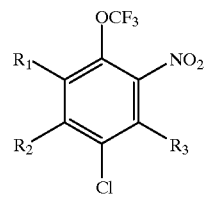

(III)

in which $R_1$, $R_2$ and $R_3$ are as defined above b) reducing the compound of formula III in order to form the compound of formula IV:

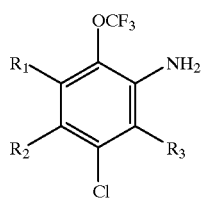

(IV)

in which $R_1$, $R_2$ and $R_3$ are as defined above c) subjecting the compound obtained in b) to a dehydrochlorination in order to obtain the compound of formula I; and d) isolating the compound obtained in step c) from the reaction mixture.

Step a) is advantageously carried out by reacting the compound of general formula II with nitric acid in sulphuric acid medium, in a protic solvent, for example acetic acid, or an aprotic solvent, advantageously a chlorinated solvent, for example dichloromethane, or without a solvent.

The reaction temperature is within the range from 0 to 60° C., the reaction preferably being carried out between 20 and 40° C.

After step a), where appropriate, the positional enantiomers obtained are separated in order to isolate the 2-nitrotrifluoromethoxyphenyl compound.

Step b) is advantageously a catalytic hydrogenation in the presence of Raney nickel in a solvent such as an alcohol or acetic acid.

As a variant, the nitro function can be reduced to amino according to a Béchamp reaction in the presence of Fe, in hydrochloric acid medium in acetic acid or in water, as solvent.

Another variant consists in reducing the compound of the preceding step with $SnCl_2$ in hydrochloric acid medium in ethanol, by heating the reaction medium at reflux for a period ranging from one to several hours.

Step c) can be carried out by hydrogenation of the compound of step b) in the presence of Raney nickel, using an alcohol or acetic acid as solvent.

Steps b) and c) can be carried out simultaneously.

Step a) is optional but preferred, any other method for obtaining the compound of formula II being acceptable.

The starting materials are known compounds which can be prepared simply.

For example, 4-chlorotrifluoromethoxybenzene can be prepared, for example, from p-chlorophenol as described in ZHUR.OBSHCHEI.KHIM. (31) 1961, p. 915–924, (CA C55) 23408); J. Org. Chem. (29), 1964, p.1–11.

As compounds of formula II, those compounds are preferred in which $R_1$, $R_2$ and $R_3$ represent hydrogen or $R_2$ and $R_3$ represent chlorine, $R_1$ being a hydrogen atom.

The advantage in the latter case is the selectivity of the reaction of step a) and thus the absence of a need to carry out a subsequent step of separation of the isomers.

The preparation of 2-trifluoromethoxyaniline from 4-chlorotrifluoromethoxybenzene will be described below more particularly.

EXAMPLE

1. Synthesis of 4-chloro-2(-3)-nitrotrifluoromethoxybenzene 1207.0 g of 4-chlorotrifluoromethoxybenzene are added over one hour to a stock of 1640 g of 96.8%-sulphuric acid and 680.4 g of 100% nitric acid, preheated to 40° C. The reaction mass is then heated to 50° C. and maintained at this temperature for four hours. After stopping the stirring, the upper organic phase is decanted off at 40° C. and then poured into 638.2 g of 18.2% caustic soda. After a further decantation, the organic phase is washed with 250 ml of water. The crude reaction mass contains a 50/50 mixture of 4-chloro-2-nitrotrifluoromethoxybenzene and 4-chloro-3-nitro-trifluoromethoxybenzene (weight: 1550 g -aniline purity: 91.8%). The nitration yield is 96%.

2. Synthesis of 2-amino-4-chlorotrifluoromethoxybenzene 10 g of Raney nickel with a moisture content of 50% in 170 ml of methanol are loaded into a 500 ml autoclave. After flushing the autoclave with hydrogen, the reaction mass is heated to 50° C. and the hydrogen pressure is adjusted to 12–13 bar. 107.0 g of 2-nitro-4-chlorotrifluoromethoxybenzene are then added continuously to the reaction mass over 1n30 to 2 hours. After addition of the nitro compound, the reaction mass is maintained at 50° C. for 30 minutes to 1 hour. The reaction mass of 2-amino-4-chlorotrifluoro-methoxybenzene thus formed is used directly in the dehydrochlorination step.

3. Synthesis of 2-trifluoromethoxyaniline 68.5 g of 30.2% caustic soda are introduced over 15 minutes into the above reactor containing the crude reaction mass, and at 12–13 bar of hydrogen, while maintaining the temperature of the reaction mass at 50 to 70° C. The reaction mass is then maintained at 70° C. for six hours. After this period, the dehydrochlorination is complete and the reaction mass is cooled to room temperature and 100 ml of water are then added. The catalyst is then filtered off and the two-phase filtrate is next heated to 100° C. in order to remove the methanol. The decantation residue is then decanted to give 77.7 g of crude 2-amino-trifluoromethoxybenzene of 96.9% titre (chemical yield: 96%). The crude product is then distilled under vacuum (64° C. at 20 torr) to give 2-aminotrifluoro-methoxybenzene in a titre of greater than 99%.

This same procedure can be carried out on the 50/50 mixture of 4-chloro-2-nitrotrifluorometh-oxybenzene and 4-chloro-3-nitrotrifluoromethoxybenzene. A mixture of 2-aminotrifluoromethoxybenzene (2-trifluoromethoxyaniline) and 3-aminotrifluoromethoxybenzene (3-trifluoromethoxyaniline) is thus obtained. These two anilines are then separated by distillation under vacuum (respective boiling points at $2.7 \times 10^3$ Pa (20 torr): 64 and 89° C.)

What is claimed is:

1. A method for the preparation of a compound of formula I

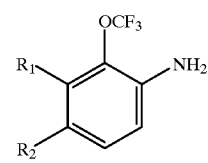

in which $R_1$ and $R_2$, which may be identical or different, represent a hydrogen atom, a $C_1$–$C_6$ alkyl group, or $R_1$ and $R_2$, taken together with the carbon atoms to which they are attached, represent a $C_6$–$C_{10}$ aryl group; comprising the following steps:

a) optionally reacting a compound of general formula II:

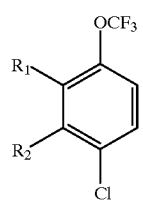

in which $R_1$ and $R_2$ are as defined above or $R_1$ represents a hydrogen atom or a $C_1$–$C_6$ alkyl group, or $R_1$ and $R_2$, taken together with the carbon atom to which they are attached, represent a $C_6$–$C_{10}$ aryl ring, with a nitration reagent in order to form a compound of formula III:

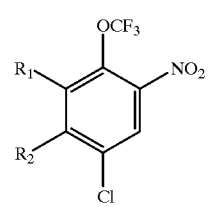

in which $R_1$ and $R_2$ are as defined above b) reducing the compound of formula III in order to form the compound of formula IV:

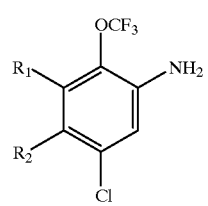

in which $R_1$ and $R_2$ are as defined above c) subjecting the compound obtained in b) to a hydrogenolysis in order to obtain the compound of formula I; and d) isolating the compound obtained in step c) from the reaction mixture.

2. A method according to claim 1, wherein step a) comprises the reaction of the compound of general formula II with nitric acid in sulphuric acid medium in a protic or aprotic solvent or in the absence of a solvent at a temperature of between 0 and 50° C.

3. A method according to claim 1, wherein step b) comprises a catalytic hydrogenation in the presence of Raney nickel.

4. A method according to claim 1, wherein step c) is a catalytic hydrogenation in the presence of Raney nickel.

5. A method according to claim 1, comprising preparing 2-trifluoromethoxyaniline from 4-chlorotrifluoromethoxybenzene.

* * * * *